United States Patent
Marty et al.

(10) Patent No.: US 8,859,289 B2
(45) Date of Patent: *Oct. 14, 2014

(54) METHOD AND LABORATORY SYSTEM FOR HANDLING SAMPLE TUBES AND AN IMAGE ANALYZING UNIT

(75) Inventors: Christian Marty, Rotkreuz (CH); Markus Rinderknecht, Adligenswil (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 64 days.

This patent is subject to a terminal disclaimer.

(21) Appl. No.: 12/460,761

(22) Filed: Jul. 23, 2009

(65) Prior Publication Data
US 2010/0018330 A1 Jan. 28, 2010

(30) Foreign Application Priority Data
Jul. 25, 2008 (EP) .................................. 08013458

(51) Int. Cl.
*G01N 1/00* (2006.01)
*G06K 9/00* (2006.01)
*G01N 35/04* (2006.01)
*G01N 35/00* (2006.01)
*G01N 35/02* (2006.01)

(52) U.S. Cl.
CPC .......... *G01N 35/04* (2013.01); *G01N 35/00594* (2013.01); *G01N 35/0099* (2013.01); *G01N 35/02* (2013.01); *G01N 35/00732* (2013.01); *G01N 35/028* (2013.01); *G01N 2035/0425* (2013.01)
USPC ................... 436/48; 436/43; 422/65; 422/67; 73/864.81

(58) Field of Classification Search
None
See application file for complete search history.

(56) References Cited

U.S. PATENT DOCUMENTS

| 5,721,384 | A | 2/1998 | Tanihati ..................... 73/864.81 |
| 5,985,215 | A | 11/1999 | Sakazume et al. ............... 422/67 |
| 6,068,437 | A | 5/2000 | Boje et al. ................ 414/331.02 |
| 6,220,451 | B1* | 4/2001 | Hoffmann ..................... 209/522 |
| 6,599,476 | B1 | 7/2003 | Watson et al. .................. 422/63 |
| 6,926,058 | B2* | 8/2005 | Sato et al. ..................... 156/556 |

(Continued)

FOREIGN PATENT DOCUMENTS

| EP | 0 467 302 | 1/1992 | |
| EP | 1348965 | 10/2003 | ............. G01N 35/04 |

(Continued)

OTHER PUBLICATIONS

Extended European Search Report in EP 08013458, dated Jan. 7, 2009.

(Continued)

*Primary Examiner* — Yelena G. Gakh
*Assistant Examiner* — Michelle Adams
(74) *Attorney, Agent, or Firm* — McDonnell Boehnen Hulbert & Berghoff LLP (57) ABSTRACT

A method and laboratory system for handling sample tubes and an image analyzing unit are disclosed. An incoming primary rack (PR) containing sample tubes (S) is transferred to an image analyzing unit (310). Geometry parameters of at least one sample tube contained in the primary rack are determined by means of image analyzing and compared with predetermined geometry criteria. If the sample tube's geometry fulfils the criteria, the sample tube is categorized as system conform and removed from the primary rack with a gripper for further processing; otherwise it is categorized as non-system conform and entered into error processing.

10 Claims, 8 Drawing Sheets

(56) References Cited

U.S. PATENT DOCUMENTS

| | | | |
|---|---|---|---|
| 7,364,907 B2 * | 4/2008 | Weselak et al. | 436/43 |
| 2002/0023444 A1 | 2/2002 | Felder et al. | 62/177 |
| 2004/0213651 A1 | 10/2004 | Malin | 414/331.05 |
| 2005/0053454 A1 | 3/2005 | Wiggli et al. | 414/752.1 |
| 2007/0014469 A1 * | 1/2007 | Paillet et al. | 382/159 |
| 2007/0172396 A1 | 7/2007 | Neeper et al. | 422/104 |
| 2009/0142844 A1 * | 6/2009 | Le Comte | 436/8 |

FOREIGN PATENT DOCUMENTS

| | | | |
|---|---|---|---|
| EP | 1353183 | 10/2003 | G01N 35/10 |
| EP | 1391402 | 2/2004 | B65G 1/04 |
| JP | 09133687 | 5/1997 | |
| JP | 2002040034 A | 2/2002 | |
| JP | 2002090374 A | 3/2002 | |
| JP | 2003083991 A | 3/2003 | |
| WO | 83/00393 | 2/1983 | |
| WO | WO99/28724 | 6/1999 | G01N 1/00 |

OTHER PUBLICATIONS

Handbook of Clinical Automation, Robotics and Optimization, G. Kost ed., Chapters 12 and 13, Wiley & Sons, Inc. (1996).

* cited by examiner

METHOD AND LABORATORY SYSTEM FOR HANDLING SAMPLE TUBES AND AN IMAGE ANALYZING UNIT

TECHNICAL FIELD

The present invention relates to the handling of sample tube racks in a test laboratory environment, and particularly to a laboratory device for handling sample tubes in the context of storing such sample tubes in a storage compartment. More particularly, the present invention relates to an automated tubes identification system.

DESCRIPTION OF THE RELATED ART

In laboratories, such as for example clinical laboratories in which patient samples are examined and submitted to various in-vitro diagnosis tests, test tubes containing samples (such as blood, urine, etc.) have to be handled in high number and in a cautious but still efficient manner. For years now, automated procedures with corresponding systems and devices have been used in this context.

One aspect during the handling of these sample tubes relates to the tubes being placed in a storage compartment, which can be, for example, a refrigerating device. For efficient handling purposes, the tubes are not handled individually but placed in so-called racks. Usually, the tubes are placed in the racks already by the client, i.e., the person, the department or the institution sending samples to the laboratory, and are then sent or transported to the laboratory in these racks. In the laboratory, the racks with the tubes are subject to further handling steps for testing. Very often, such racks contain tubes with different sizes, heights, diameters, contents, expiration dates of the samples etc., which complicates automated handling so that in some cases further automated insertion of the racks in the test process in the laboratory is not possible, the racks having to be discharged manually.

U.S. Pat. No. 5,985,215 discloses transferring of sample racks, in each of which a plurality of sample containers are held, from a rack feeding unit to a discrimination unit for discriminating a type of each sample container. After the discrimination unit, a plurality of analysing units are installed along a transfer line, and pipetters of different types are provided in the respective analysing units. The discrimination unit detects information on the length and the width of each sample container held in each sample rack by using an optical detector. A control part selects one of the analysing units, suitable for analysing the sample container of which type was discriminated, based on the information detected by the discrimination unit, and transfers the sample container of which type was discriminated, to a sample pipetting position in the selected analysing unit.

Document WO 99/28724 A1 discloses a pathology distribution system for automated sample containers distribution. The system comprises a loading station for loading samples in primary containers of different types, a sample handling station for receiving the containers and identifying the container types and samples therein, and a container distribution station for distributing the containers in areas or racks in the distribution station marked for analysing processes prescribed for the samples therein. The handling station includes an image analyser for imaging the shape and colour of the cap on a container and/or other characteristic parts of the container for identifying the type of the container, and the sample in the container for determining the level and the volume of the sample available for aspiration if required. It also has a bar code reader for identifying the sample in the container. To this end, the image analyser comprises a digital camera which captures the dimensions of a tube. Further, a number of windows within the field of view of the camera are defined for capturing images of parts of the tube. In addition, a pair of windows are defined for capturing respective contrasting black and white colour patches arranged in fixed positions in front of the camera. The images captured through the plurality of windows are compared to stored images of corresponding windows using an algorithm. For imaging, however, the known system has to handle and examine single containers.

SUMMARY

In one aspect, a method for handling laboratory sample tubes is disclosed. Sample tubes contained in an incoming rack (referred to herein as a "primary rack") are analysed by means of an image analysing unit. Based upon data from the image analysis, the sample tubes' geometry parameters are determined, and it is determined (in an identification and allocation unit 42 which might be part of a CPU (central processing unit) 40 connected to the laboratory system 10 of the invention) whether an analysed tube fulfils predetermined geometry criteria. In case of non-fulfilment of the predetermined criteria, the sample tube is categorized as non-system conform and allocated an according designation by the identification and allocation unit. Each sample tube identified as system conform is entered into further processing and each sample tube identified as non-system conform is entered into error processing. Particularly, each sample tube identified as system conform may be sorted into a so-called secondary rack (such as, for example, a storage rack or another standardised rack compatible with the system requirements) for further processing.

Thus, in the method, it is determined whether an analysed sample tube inserted in the laboratory system meets given geometry criteria. Based upon this determination, the sample tube is either categorized as system conform or non-system conform and further processed accordingly. This facilitates the automated handling of sample tubes as there is no typing according to known types of sample tubes as such a comparison proves to be error-prone. Also, in case of new types of tubes emerging, the data base of the system has to be updated. According to the invention, the set of geometry criteria only has to reflect compliance of the sample tubes with system requirements and has not to be changed if new kinds of tubes are used. As a further advantage, sample tubes do not have to be taken out of the primary rack for the analysis but rather can be analysed in their rack position. This allows faster processing and analysis of all tubes in one rack in a short time span or even at once. Particularly, examination of the sample tubes while being placed in the primary rack avoids any handling of tubes by means of a gripper when they are not in compliance with the system requirements. As a result, system robustness is enhanced because the handling of non-compliant or non-conform tubes with a gripper could lead to collision with the sample tube and resulting breakage or unsuccessful handling actions.

According to one embodiment, the predetermined geometric criteria may comprise any one of the criteria of the group consisting of tube diameter, tube height, angle of position of the tube in the primary rack, presence of a tube cap and a spreading barcode label on the tube. The analysis may proceed in the order given above or in any other order. Of course, the invention is not limited to the cited criteria, and other geometry parameters may be included in the list of criteria of the person skilled in the art.

Further, it may be provided that a sample tube which is found to be non-system conform is allocated a non-conformity designation. Sample tubes identified/designated as non-system conform are entered into error processing. There are errors which can be cured by the system, as e.g. a no-cap designation. There are also errors which cannot be cured by the system, as, e.g., a tube not in compliance with the required geometrical parameters. In the latter type of errors, error processing may cause the system to transfer the corresponding rack with the non-system conform sample tube to an error position, e.g., for further manual handling, for returning the sample tube to its origin, for disposal etc. According to the invention, a sample tube which is identified as non-system conform is not taken out of the primary rack, i.e., no further handling (in particular no gripping) of this sample tube will be done, thus reducing the risk of damaging or breaking a tube. Non-system conform tubes are more likely to be crashed as they do not comply with the (geometric) system requirements. As a consequence breakages and spilling of sample fluids such as blood can be significantly reduced. Non-system conform tubes are left in their rack and error processing can be performed by handling the rack instead of handling a non-system conform sample tube. Other sample tubes in the same rack can be further processed (in particular removed from the rack) in advance of error processing of the non-system conform sample tube.

In another case which initiates error processing, the sample tube is found to have no cap (which is one possible geometry criterion), the non-conformity designation may be a no-cap designation. The presence of such a no-cap designation may cause the system to transfer the according sample tube individually or preferably in its primary rack (alone or together with the other sample tubes of this rack notwithstanding their designation status) to a capping station for automated re-capping of the sample tube. In order to prevent tubes with a diameter too small or too large for the capping station from being transferred to the capping station, transfer to the capping station may occur only after it has been established whether the sample tube fulfils the diameter criterion. Transfer of the racks and tubes is performed in automated manner by a transfer unit which can comprise one or more conveyors, one or more transfer belts and/or one or more robotic arms or any other suitable transfer device. When a sample tube without cap has been capped the non-conformity designation for this tube may be changed in a conformity designation provided that it fulfils the other conformity requirements and the tube may be processed further as described herein.

Further features and embodiments will become apparent from the description and the accompanying drawings.

It will be understood that the features mentioned above and those described hereinafter can be used not only in the combination specified but also in other combinations or on their own, without departing from the scope of the present disclosure. The disclosure of the invention also covers the corresponding methods of operation of the disclosed devices and systems, and the present description also covers a computer program with program coding means which are suitable for carrying out the methods of the invention when the computer program is run on a computer or control unit. The computer program itself as well as stored on a computer-readable medium is claimed.

Various implementations are schematically illustrated in the drawings by means of an embodiment by way of example and are hereinafter explained in detail with reference to the drawings. It is understood that the description is in no way limiting on the scope of the present disclosure and is merely an illustration of a preferred embodiment.

DETAILED DESCRIPTION

Reference will now be made in detail to some embodiments, examples of which are illustrated in the accompanying drawings. Wherever possible, the same reference numbers are used throughout the drawings to refer to the same or like parts.

Figure 1:
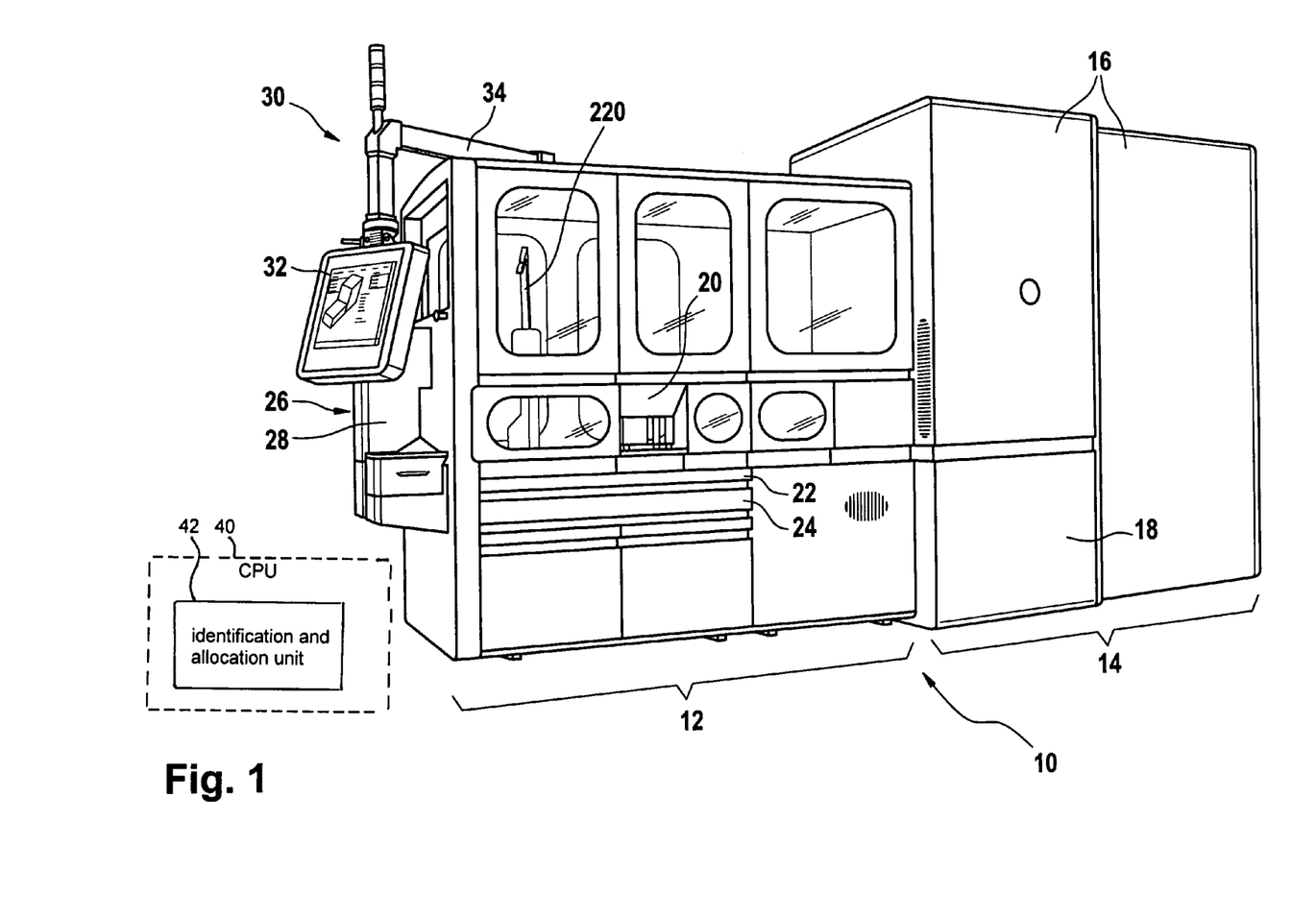
FIG. 1 shows a perspective view of a laboratory equipment unit comprising a laboratory system in which the invention can be practiced.

FIG. 1 shows a perspective view of a laboratory equipment unit 10 comprising a laboratory system in which the invention can be practiced. This laboratory equipment unit 10 may be a so-called storage retrieval module (SRM) forming part of an overall laboratory analyser system. The storage retrieval module comprises a rack handler section 12 (on the left hand side of the depiction of FIG. 1) and a refrigerating or cooling section 14 (on the right hand side of the depiction of FIG. 1). Between the two sections 12, 14 there is a loading/unloading interface (not shown) through which racks are transferred from the the rack handler section 12 into the refrigerating or cooling section 14 and back (in case of retrieval). This loading/unloading interface may be designed like a gate or the like.

The storage section 14 may comprise a refrigerator 16. A storage section in the context of this invention is a cabinet of various size which is able to store a plurality of sample tubes in storage racks. The storage section may have a cooling unit to hold the ambient temperature for the tubes within the storage section below room temperature, possibly below 18° C. and possibly below 10° C.

In its inside, the storage section 14 comprises a plurality of shelves for storage of a high number of sample tube racks. The sample tube racks loaded into the storage section are referred to herein as "storage racks," i.e., standardized racks. This implies that all tubes contained in primary racks (i.e., incoming racks of various types) fulfilling the geometry criteria of the invention are taken out of their respective primary racks and are re-sorted in suitable storage racks before being loaded into the storage section 14. The storage section may be large enough for one or two human beings being able to enter the inside of the storage section 14 through a door (not shown). In case the door is opened, a safety switching circuit ensures that all moving systems (like robotic arms or other transfer or conveying systems) come to a standstill, for example in a neutral or home position. While primary racks are single-row racks with somewhat standard geometry and therefore easy to handle in a plurality of different laboratory systems, the secondary racks and particularly the storage racks are multi-row racks (e.g., three rows with more than ten positions, for example 13 to 14 positions). Therefore, the secondary racks are more stable, particularly for storing purposes, and less likely to tilt over.

Further, the storing section 14 may comprise a disposal unit 18. The disposal unit 18 is connected with the storage section 14 via an internal opening (not shown) in a wall separating the storage section 14 from the disposal unit 18. Through this opening, sample tubes whose expiration date (i.e., shelf life) has elapsed can be disposed automatically in the disposal unit 18.

The rack handler section 12 has a housing consisting of several outer walls with windows so that operating personnel can have a direct visual overview of the rack handler's functioning. The rack handler section 12 comprises an opening 20 in one of the outer walls through which primary racks can be inserted into the storage retrieval module 10. The opening 20 leads to the rack handling area 210 (cf., FIG. 2) which comprises at least one robotic arm 220 (which can be seen in the depiction of FIG. 1 through one of the windows). The opening 20 might be closable by means of a sliding or retractable door (not shown).

The rack handler section 12 further comprises drawers 22, 24 through which emptied primary racks and/or primary racks containing sample tubes with error designations and/or racks containing at least one retrieved sample tube can be taken out of the storage retrieval module 10. It may be preferred to define distinct output sections for the various mentioned outputs (i.e., error racks, empty racks, racks with tubes for additional testing or re-testing) in order to avoid mistakes due to confusion.

Further, the rack handler section 12 comprises a capping station 26 with a feeder tank 28 for tube caps.

The storage retrieval module 10 also comprises a man-machine interface (MMI) 30 which might have the form of a touch screen monitor 32 at the end of an articulated arm 34.

Figure 2:
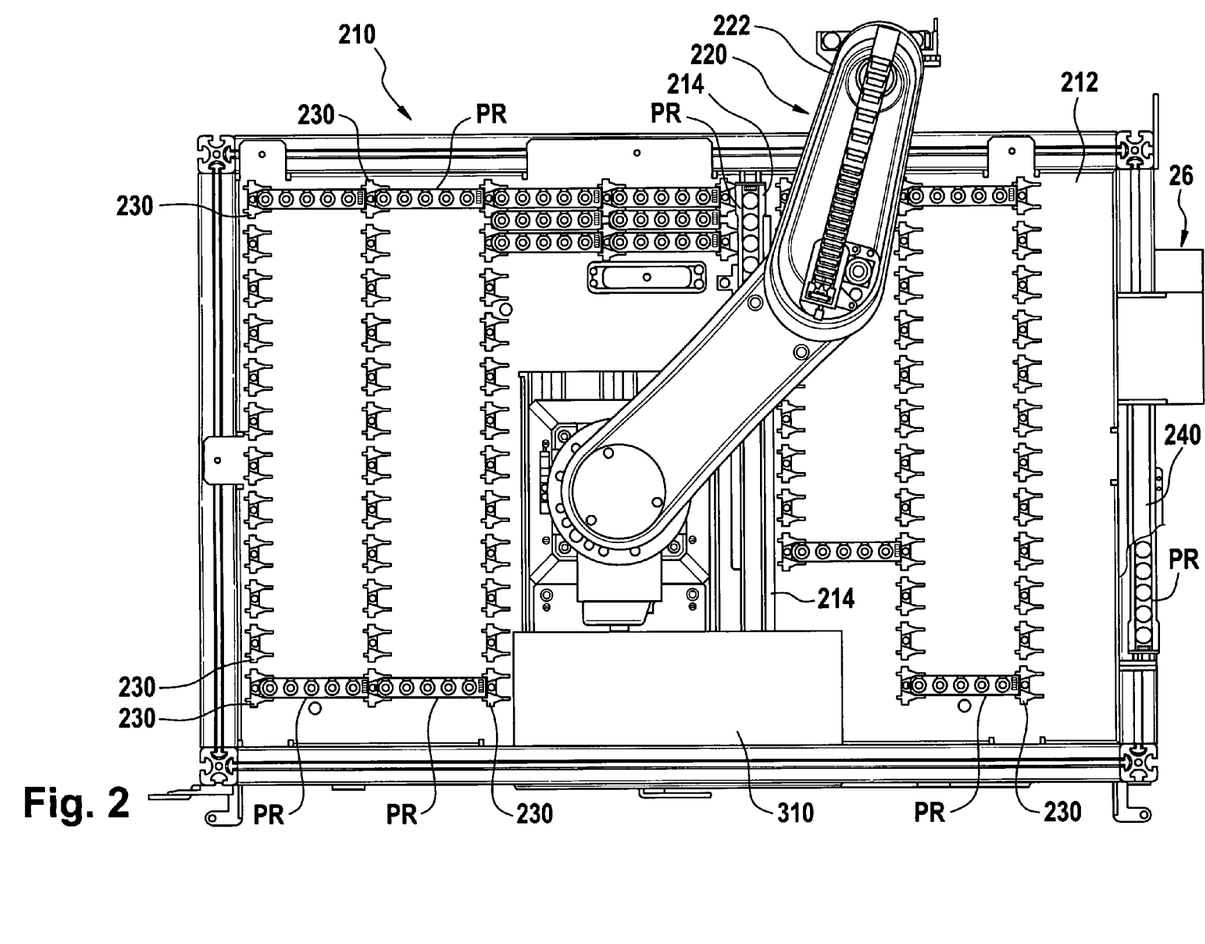
FIG. 2 shows a top view on a rack handler area of the laboratory system of FIG. 1.

FIG. 2 shows a top view of the rack handler area 210 of the laboratory system of FIG. 1. The rack handler area 210 comprises a platform 212 inside the rack handler section 12 of FIG. 1. It further comprises a robotic arm 220 which may be installed essentially in the centre of the platform 212 or at least at a position from which it can reach at least all locations within the rack handler area 210. Any known suitable robot can be used for this purpose, such as for example a SCARA robot with four axes and four degrees of freedom. The robotic arm 220 comprises, at its end, a gripper 222 designed to securely grip the racks to be handled.

On the platform 212, a conveyor 214 is provided for conveying incoming primary racks PR containing sample tubes (e.g., five sample tubes) to an image analysing unit 310 (cf., FIG. 3) which is also positioned on the platform 212.

Further, a plurality of alignment elements 230 are provided on the platform 212. The alignment elements 230 are designed to hold in place the primary racks PR in a desired alignment or orientation which corresponds to an orientation of the gripper 222 of the robotic arm 220. The alignment elements 230 define an area for interim parking or stocking of primary racks on the platform 212. While any kind of primary racks compatible with the geometry of the alignment elements can be parked here, preferably so-called standardised primary racks are stocked in this area in order to be loaded with sample tubes retrieved from the storage section 14 because they are needed for additional tests or for retesting.

Figure 3:
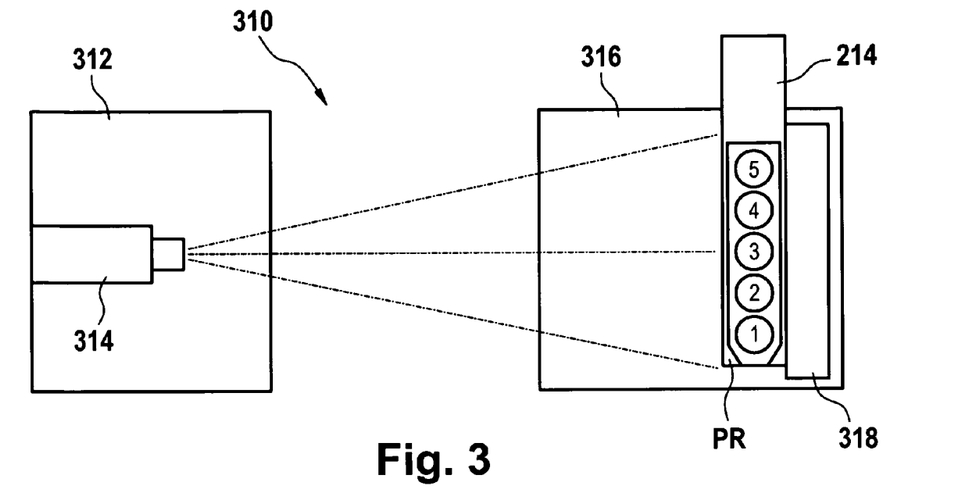
FIG. 3 shows a schematic top view of the image analysing unit of FIG. 2.
Figure 4:
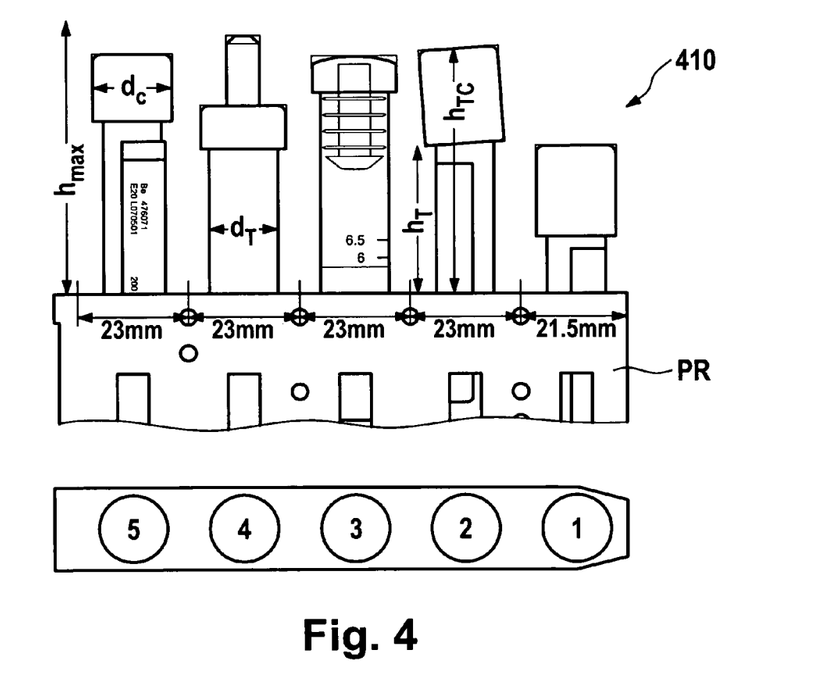
FIG. 4 shows an image of a primary rack containing five sample tubes with added geometry criteria.

In order to ensure proper orientation of the primary racks PR in every step of processing (such that sample tubes positions 1 to 5 are always unambiguously identifiable; cf., FIGS. 3 and 4), the primary racks may not be introduced directly on the conveyor 214 through the opening 20 but rather be taken up by the gripper 222 of robotic arm 220 and then placed on the conveyor 214. For this, a receiving position (not shown) for incoming racks is provided from which the robotic arm then takes up the incoming rack in order to place it onto the conveyor 214 in a desired orientation. For this the robotic arm may be equipped with an orientation detector for determining the orientation of the gripped rack relative to the gripper. Alternatively the orientation of the rack and the position of vessels in the rack may be determined based on geometrical parameters in the image analysing unit.

As shown in FIG. 3, the image analysing unit 310 comprises a first housing 312 in which a camera 314 is positioned, and a second housing 316 in which the conveyor 214 is leading in such a manner that a primary rack PR is conveyed into the second housing 316 into a predetermined position (examination position) in front of a backlight 318 providing homogenous lighting. The second housing 316 has the function of a light tunnel protecting the primary rack from extraneous light during image recording. The camera 314 is positioned so that it focuses on the predetermined rack position in front of backlight 318 and takes an image 410 (cf., FIG. 4) of at least all five sample tubes 1 through 5 in the primary rack PR, and also at least the upper portion of primary rack PR, as can be seen in FIG. 4. In order to further improve homogeneity of the illumination, the background lighting may be provided with a light homogenisator, e.g., a ground-glass screen.

The image 410 taken by the camera 314 is analysed as to various predetermined geometry parameters of the sample tubes 1 to 5 according to predetermined geometry criteria. The image analyser (which can be any suitable analyser of known type) can find and identify the various sample tubes 1 to 5 due to predetermined and known distances between the locations (23 mm in the shown example; only location 1 in the primary rack PR has a smaller width of 21.5 mm due to the shape of the primary rack which helps identify proper orientation of the rack).

One of the parameters to be analysed is the height of the sample tube above the upper edge of the primary rack PR. The total height of the sample tube including cap is defined as $h_{TC}$, and the height of the sample tube without cap is defined as $h_T$.

Another one of the parameters is the diameter of the sample tube which is defined as $d_T$. Still another parameter is the diameter of the cap which is defined as $d_C$. Presence of cap can be identified by determining whether $d_C > d_T$ and/or whether $h_{TC} > h_T$. Alternatively, presence of a cap can be identified by determining the difference of brightness of two measuring fields, a reference field outside the cap and a measuring field inside the cap, or determination of a top tube line.

A further parameter is the angle of the sample tube in the rack, i.e. its inclination to the vertical which is the desired or optimum position. The angle can be determined by first determining the longitudinal axis of the tube by means of image analysing and then determining the angle between the longitudinal axis and the vertical. The angle of a sample tube in the rack is important to know as a sample tube which is too much inclined cannot be taken up by the gripper of the robotic arm properly and it might be broken by the gripper or might fall down and get smashed. Any breakages and smashes have to be avoided as this would result into a spilling of the contained fluid which is, very often, blood.

One further parameter is whether the barcode label which is applied to the outer surface (shell) of each tube is properly applied or sticking out (i.e. whether there is a spreading barcode label). This can be determined by checking if the diameter $d_T$ of a sample tube is constant all over its height $h_T$. Any deviation from a constant diameter might be an indication of a spreading barcode label. This is important to know as sample tubes with spreading barcode label are a hazard to handle, particularly when taking them out of the primary rack (where the sample tube might have got stuck due to the spreading barcode label) or when they are placed into another rack (which might not be possible because of the label material being in the way so that the tube cannot be inserted in the available opening of the target rack).

Figures 8, 9:
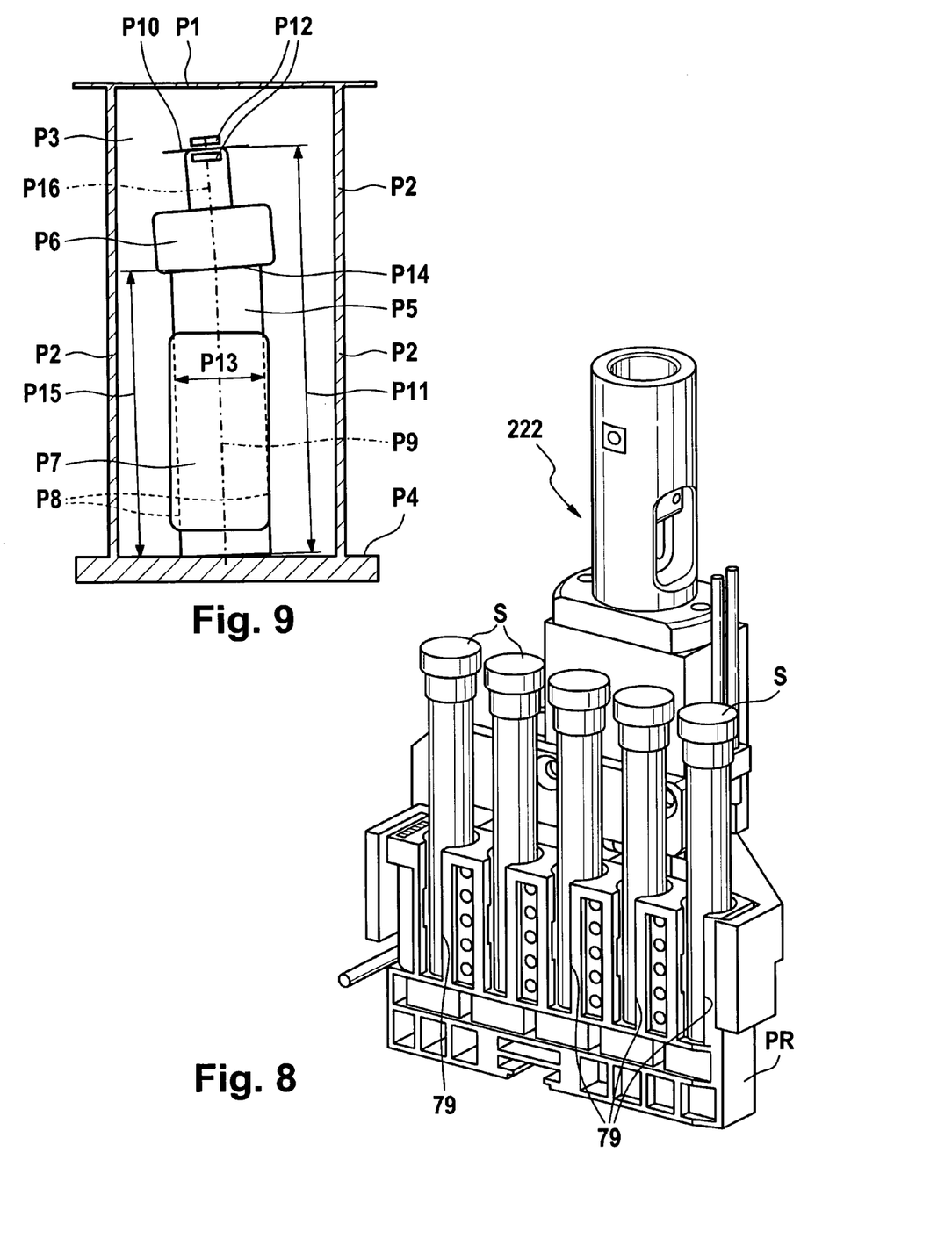
FIG. 8 shows a front perspective view of a gripper of a robotic arm holding a primary rack.
FIG. 9 illustrates various geometric criteria of a sample tube to be analysed.
Figure 10:
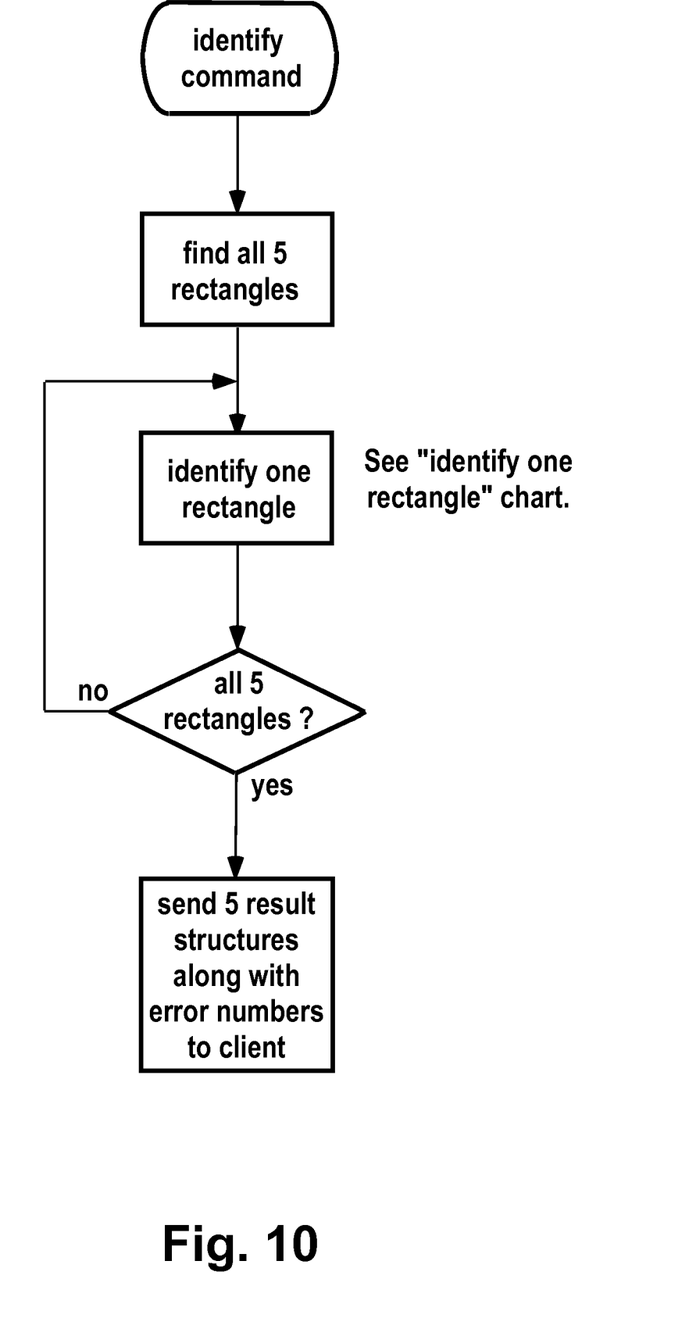
FIG. 10 shows a first flow diagram for tube identification.
Figure 11:
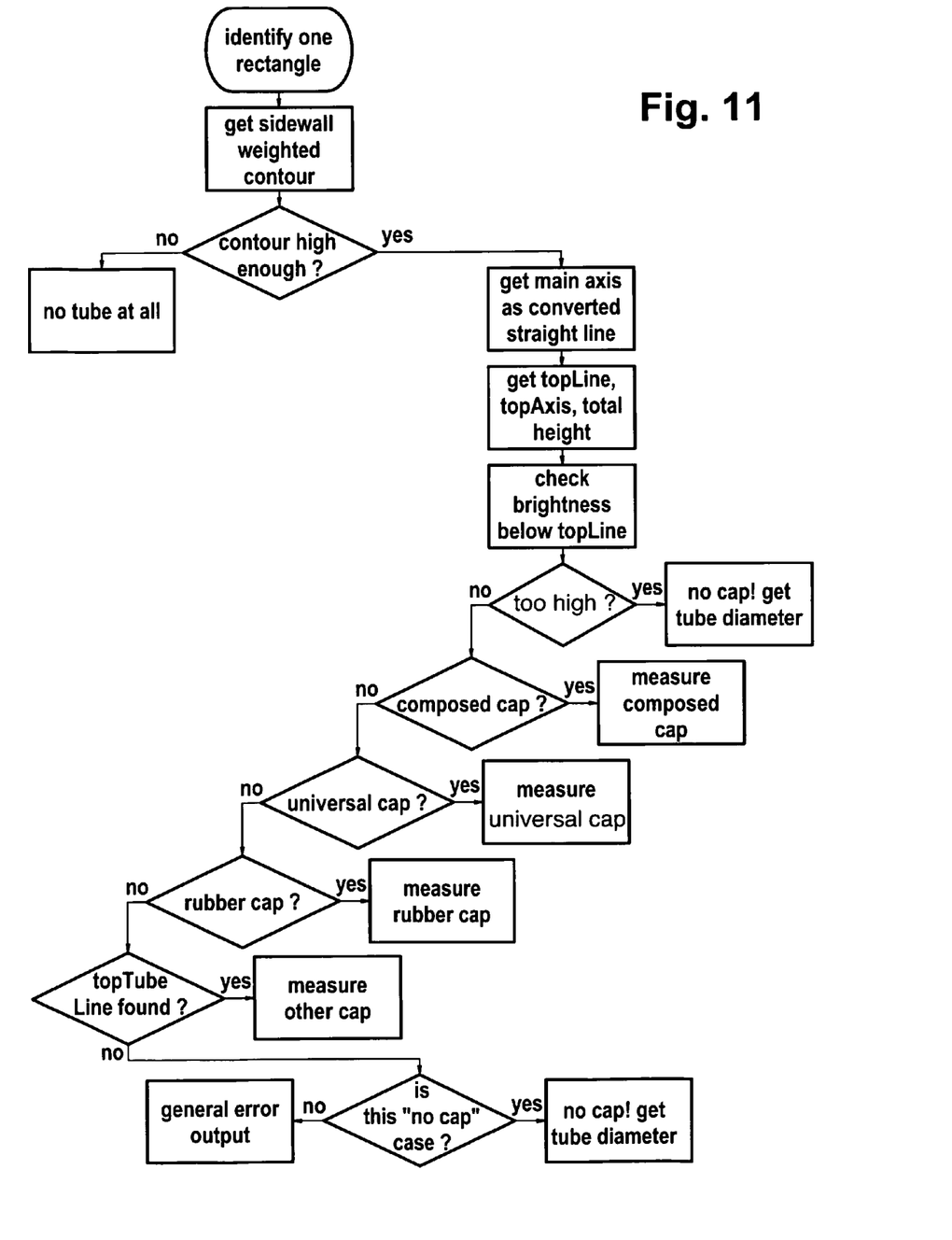
FIG. 11 shows a second flow diagram for tube identification.

FIG. 9 illustrates various measuring parameters to be identified in the image analysing unit of the invention. Parameter P1 indicates the border of the backlight, parameter P2 indicates the fins, parameter P3 indicates the rectangular measuring field, parameter P4 indicates the top border of the rack, parameter P5 indicates the sample tube, parameter P6 indicates the cap, parameter P7 indicates the barcode label, parameter P8 indicates the sidewall contour (ignoring spreading labels), parameter P9 indicates the tube axis, parameter P10 indicates the top line, parameter P11 indicates the total height, parameter P12 indicates the reference and the measuring fields for brightness check, parameter P13 indicates the tube diameter, parameter P14 indicates the tube top-line, parameter P15 indicates the tube height, and parameter P16 indicates the cap axis. FIG. 10 shows a first flow diagram for the "identify command" for the identification process, and FIG. 11 shows in more detail the subcommand "identify one rectangle" from the flow diagram of FIG. 10.

Figure 5:
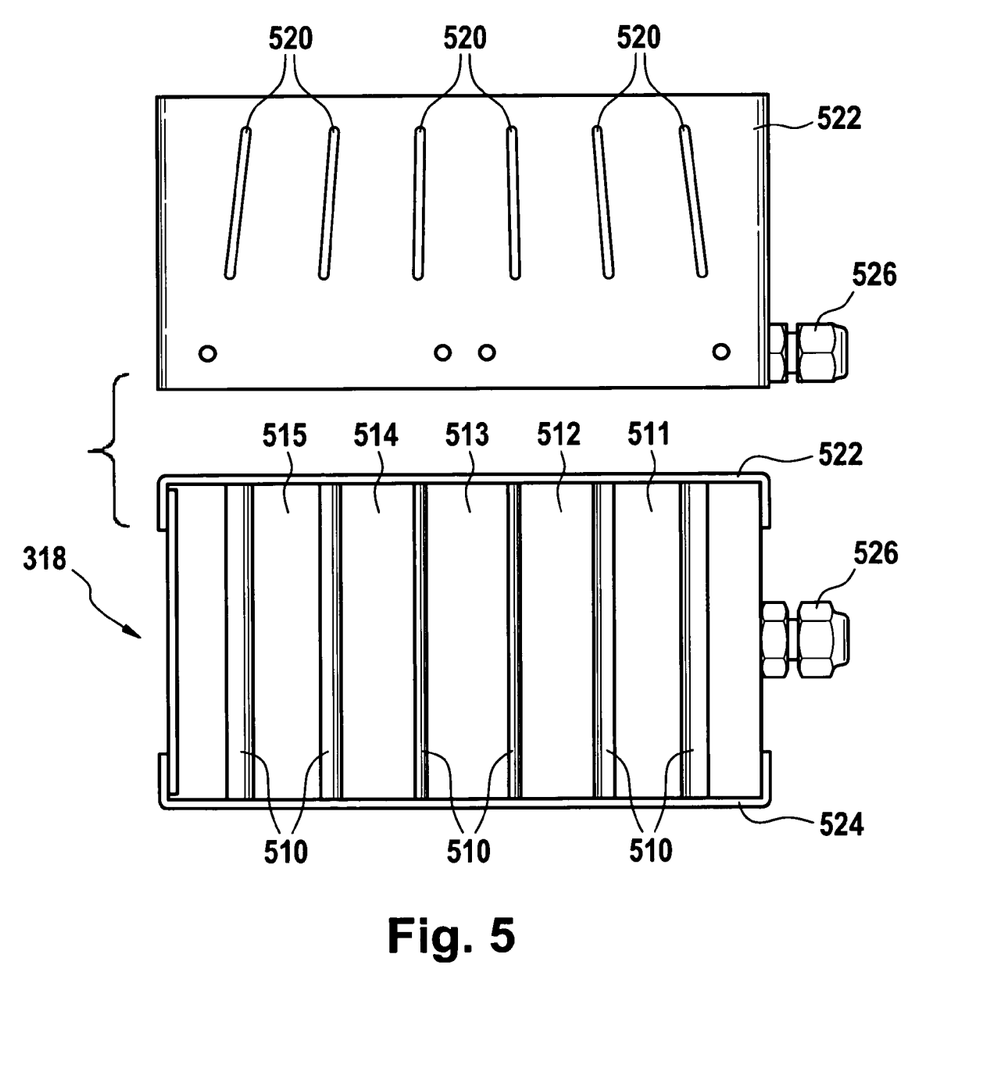
FIG. 5 shows a top and a front elevation of a backlight box of the image analysing unit of FIG. 2.

FIG. 5 shows a top (upper drawing) and a front (lower drawing) elevation of the backlight box 318 of the image analysing unit 310. The backlight box 318 may consist in its simplest version of a box with five surrounding walls and an open front towards the camera 314. The interior of the walls may be designed in such a manner to promote homogenous lighting (originating from the backlight itself) and to prevent entrance of scattered light. As can be seen from the drawings of FIG. 5, the box may further contain fins or blades 510 extending substantially vertically through the interior of the backlight box and defining visual chambers 511, 512, 513, 514, 515 for the sample tubes 1, 2, 3, 4, 5 in a primary rack PR, correlating to the tube positions in the rack.

Apart from defining visual chambers, the fins 510 also reduce scattered light from one chamber to another so that picture or image quality is enhanced. The backlight box preferably emits monochrome light, possibly in a wavelength range of a few nanometers. The camera may record a grey value picture.

The fins 510 are positioned in slots 520 which are provided in a top wall 522 of the backlight box 318 (according slots may also be provided in the bottom wall 524 for better fixation of the fins). As can be seen, the fins 510 are not positioned in parallel to each other but with an angle adapted to the optical path of the lens of camera 314 in order to be aligned therewith. This means that on a picture or image taken by camera 314, each fin can be seen as a line delimiting a visual tube chamber from another, therefore facilitating the determination of presence of sample tubes in a given rack position and identification of the sample tubes. For the sake of good order and clarity, it has to be noted that no fins are visible in the exemplary image of FIG. 4.

On the right hand side in the drawings of FIG. 5, a port 524 for the electrical wiring for the backlight 318 is shown.

In operation, a primary rack PR is inserted into the second housing 316 within the image analysing unit 310 either in front of the fins 510 or behind the fins 510 (both options are basically possible; in the latter case, the primary rack is inserted between the backlight and the fins; the first option has the advantage that the fins reduce scattered light from one chamber to another, cf. above). Correct positioning is reached when each sample tube position of the primary rack is between two respective fins 510. An appropriate opening (not shown) is provided in one of the side walls of the second housing to allow insertion of the rack by means of conveyor 214 as already described above in reference to FIG. 3.

Figure 6:
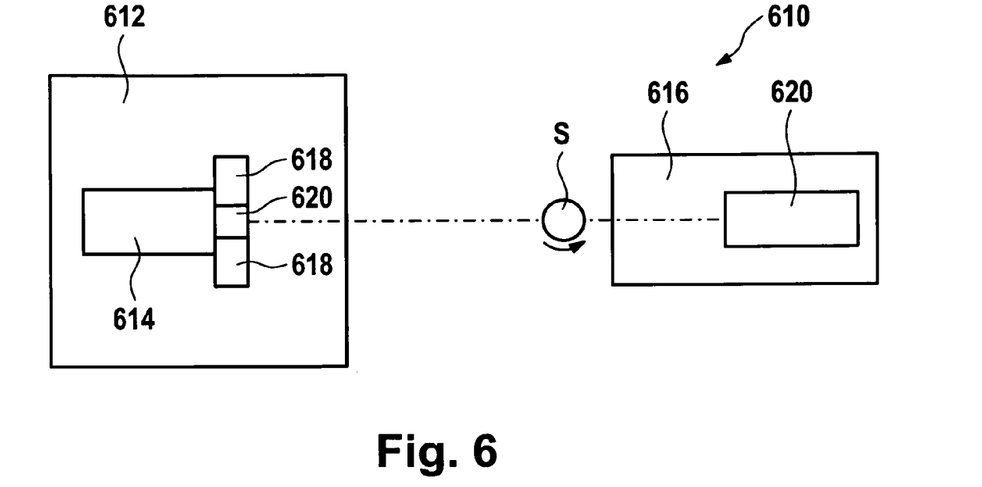
FIG. 6 shows a schematic top view of a serial image unit.
Figure 7:
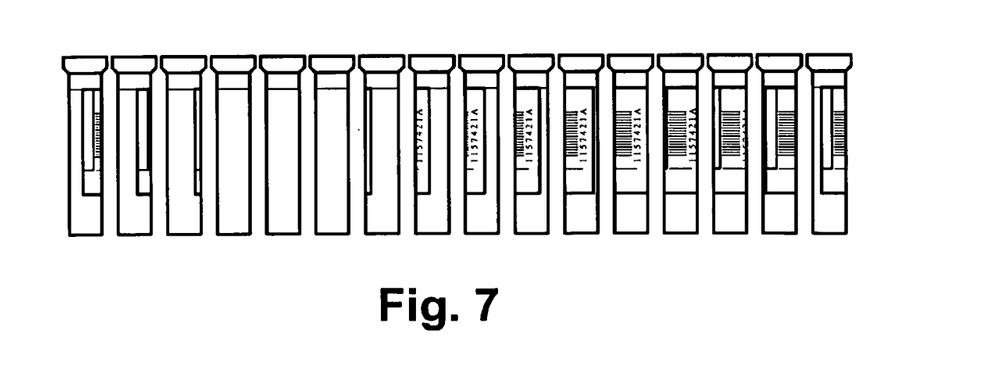
FIG. 7 shows by way of example an image taken by the serial image unit of FIG. 6.

FIG. 6 shows a schematic top view of a serial image unit 610 of the invention. The serial image unit 610 is an additional image unit, i.e. in addition to the image analysing unit 310. The purpose of the serial image unit 610 is to take a serial picture of each sample tube. A serial picture (also called roll-off picture) shows, preferably in one picture, subsequent images of a subject taken from different angles of view. This can be achieved for example by rotating the subject whose picture is to be taken and taking subsequent pictures during this rotation, preferably at given angles of rotation. Thereby, all or at least several sides of the subject can be seen in one picture. An example of such a serial or roll-off picture of a sample tube is shown in FIG. 7 which comprises 16 views covering the 360° view of the tube, i.e. a picture taken every 22.5° of rotation. Of course, not the whole range of 360° has to be taken.

Returning to FIG. 6, the serial image unit 610 comprises a first housing 612 in which a camera 614 is positioned, and a second housing 616 in which a laser scanner 620 is positioned. A light source 618 is positioned in the first housing 612 for front lighting of a sample tube S whose picture is to be taken. The light source 618 may be positioned around a lens 620 of the camera 614, and the light source 618 may be a strobe light, a flash light or a constant light. The second housing 616 is a visual cover or shield for protection against laser scanner 620. The laser scanner 620 and the camera 614 may be aligned to each other as can be seen from the drawing of FIG. 6, but they could also be placed on different optical axes as long as they both are directed on the same sample tube S during rotation of the tube.

In operation, a sample tube S is placed in the optical path 622 and rotation of the sample tube S begins. Rotation can be achieved by means of a robotic gripper, for example. The sample tube can be taken out of the rack by the gripper and then rotated and be put back into the rack at the same position after the picture is taken. Alternatively, the sample tube may be gripped by the gripper and only lifted up to an extent that at least a portion of the barcode label sufficient to be read by the scanner is located above the rack but the lower portion of the sample tube is still in the corresponding rack opening. This approach facilitates reinsertion of the sample tube in the rack after the picture is taken. As a further alternative, the sample tube is not taken out of the primary rack at all but is rather rotated while being in the rack. While this alternative does not require any handling of the sample tube at all (apart from the rotation), it requires that slots 79 in the primary rack PR (cf., FIG. 8) in front of each sample tube position be large enough so that a barcode label applied to the surface of a sample tube can be seen through the slot 79 when the sample tube is rotated in its rack position (the depiction of FIG. 6 indicates only one sample tube for exemplary purposes; in operation a whole rack with sample tubes may be inserted according to the above-mentioned alternatives).

At the same time the rotation starts, the camera starts to take a first picture which is the first (partial) still picture of the later serial picture. Triggering for the camera to take pictures may be time triggering or angle triggering (the angle could be determined from a position sensor of the robotic gripper). The serial picture can cover part or all of the 360° of the sample tube S.

Simultaneously to the rotation of the tube and the picture taking, the laser scanner scans the surface of the sample tube for a barcode label which is supposed to be attached thereto. It reads the barcode information and stores the same in a database together with the serial picture of the tube or together with a pointer or the like to the serial picture data.

After completion of the serial picture, the sample tube is further processed and stored in the refrigerator 16 of the storage section 14. Before a stored sample tube is retrieved from the storage section for possible add-on tests, an all around view of the sample tube can be obtained by retrieving the associated serial picture of the tube together with the barcode information thus allowing for an operating person to verify if the sample tube to be retrieved is the correct one. This avoids retrieving a wrong sample tube from storage.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method to handle laboratory sample tubes in a laboratory system, the laboratory system comprising a transfer unit for transferring incoming primary racks (PR) each configured for containing a plurality of sample tubes, an image analysing unit (310), and an identification and allocation unit as well as a gripper, the method comprising the steps of:
   transferring, by means of the transfer unit, an incoming primary rack (PR) containing a plurality of sample tubes to the image analysing unit (310);
   determining, in the image analysing unit (310), geometry parameters of at least one sample tube contained in the primary rack (PR) by means of image analysing, said determining step being conducted while the at least one sample tube remains in place within the primary rack (PR);
   in the identification and allocation unit, comparing for each sample tube the determined geometry parameters with predetermined geometry criteria and identifying whether the sample tube's geometry fulfils the predetermined geometry criteria;
   in case of fulfilment, categorising the sample tube as system conform;
   otherwise categorising the sample tube as non-system conform;
   wherein each sample tube identified as system conform is removed from the primary rack (PR) by the gripper and placed into a secondary rack for further processing, and each sample tube identified as non-system conform is not taken out of the primary rack (PR) and is entered into error processing.

2. The method of claim 1, wherein the predetermined geometry criteria comprise any one of the criteria of the group consisting of tube diameter, tube height, angle of position in the primary rack, presence of tube cap, and a spreading barcode label.

3. The method of claim 1, further comprising the step of allocating a non-conformity designation to the sample tube in a case where the sample tube is identified to not comply with at least one of the predetermined geometry criteria.

4. The method of claim 3, wherein the non-conformity designation is a no-cap designation in a case where the sample tube is identified to not carry any cap.

5. The method of claim 4, wherein a primary rack containing a sample tube with a no-cap designation is transferred to a capping station (26) for automated re-capping of the sample tube.

6. The method of claim 1, wherein sample tubes identified as system conform are examined by a serial image unit (610).

7. The method of claim 3, wherein in case of an allocated non-conformity designation to the sample tube, the primary rack (PR) containing such sample tube is transferred to an error position for further manual handling.

8. A laboratory system to handle laboratory sample tubes, comprising:
   one or more incoming primary racks (PR) each configured for and containing a plurality of sample tubes;
   a transfer unit for transferring said one or more incoming primary racks (PR);
   an image analysing unit (310) for analysing geometrical parameters of the sample tubes while the sample tubes remain in place in the one or more incoming primary racks (PR);
   a gripper; and
   an identification and allocation unit that is programmed with a code that when executed, causes the identification and allocation unit to:
      identify, based upon data of the image analysing unit (310), for each sample tube contained in the one or more incoming primary racks (PR) whether the sample tube's geometry fulfils a predetermined criterion;
      categorize, depending on the outcome of the identification, each sample tube as system conform in a case where the sample tube fulfils the predetermined criteria or non-system conform in a case where the sample tube does not fulfil the predetermined criteria, respectively;
      control the gripper to remove each sample tube identified as system conform from the one or more incoming primary racks (PR) to a secondary rack for further processing;
      control the gripper to leave each sample tube identified as non-system conform in the one or more incoming primary racks (PR); and
      enter each sample tube identified as non-system conform into error processing.

9. The laboratory system of claim 8, wherein the predetermined criteria comprise any one of the criteria of the group consisting of tube diameter, tube height, angle of position in the one or more incoming primary racks, presence of tube cap and a spreading barcode label.

10. The laboratory system of claim 8, further comprising a capping station (26) for automated re-capping of a sample tube identified as not carrying any cap.

\* \* \* \* \*